United States Patent
Cho et al.

(10) Patent No.: US 6,981,960 B2
(45) Date of Patent: Jan. 3, 2006

(54) CLOSED-LOOP IV FLUID FLOW CONTROL

(75) Inventors: Steve T. Cho, Santa Clara, CA (US); Gene E. Clark, Redwood, CA (US)

(73) Assignee: Hospira, Inc., Lake Forest, IL (US)

(*) Notice: Subject to any disclaimer, the term of this patent is extended or adjusted under 35 U.S.C. 154(b) by 0 days.

(21) Appl. No.: 10/727,702

(22) Filed: Dec. 4, 2003

(65) Prior Publication Data

US 2004/0087895 A1 May 6, 2004

Related U.S. Application Data

(63) Continuation of application No. 09/628,846, filed on Jul. 31, 2000, now Pat. No. 6,685,668.

(51) Int. Cl.
A61M 31/00 (2006.01)

(52) U.S. Cl. .............................. 604/65; 604/67; 604/118
(58) Field of Classification Search ................... 604/65, 604/67, 118, 251, 253, 254
See application file for complete search history.

(56) References Cited

U.S. PATENT DOCUMENTS

| | | | |
|---|---|---|---|
| 4,278,085 A | 7/1981 | Shim | 128/214 |
| 4,443,218 A | 4/1984 | DeCant et al. | 604/67 |
| 4,447,224 A | 5/1984 | DeCant et al. | 604/67 |
| 4,925,444 A | 5/1990 | Orkin | 604/80 |
| 5,342,298 A | 8/1994 | Michaels | 604/65 |
| 5,429,601 A | 7/1995 | Conley | 604/65 |
| 5,489,265 A | * 2/1996 | Montalvo et al. | 604/67 |
| 6,110,152 A | 8/2000 | Kovelman | 604/232 |
| 6,280,408 B1 | 8/2001 | Sipin | 604/65 |
| 6,539,315 B1 | * 3/2003 | Adams et al. | 702/47 |

* cited by examiner

Primary Examiner—Thomas Denion
Assistant Examiner—Jaime Corrigan
(74) Attorney, Agent, or Firm—Beth A. Vrioni; Michael R. Crabb

(57) ABSTRACT

In a cosed-loop process, a controller uses a flow sensor to monitor the flow of a medicinal fluid being infused into a patient, to achieve a desired rate of flow. A relatively inexpensive peristaltic pump or electronically controlled valve can be used to vary the flow of the medicinal fluid through a fluid line. A Y site within the fluid line includes an integral flow sensor having an orifice. The flow sensor includes proximal and distal pressure sensors disposed on opposite sides of the orifice to monitor the distal and proximal pressure, producing a signal indicative of the rate of flow of the medicinal fluid through the fluid line. A signal produced by the controller is input to a motor driving the pump or to the valve to vary the rate of flow as required to achieve the desired infusion rate of the medicinal fluid.

4 Claims, 5 Drawing Sheets

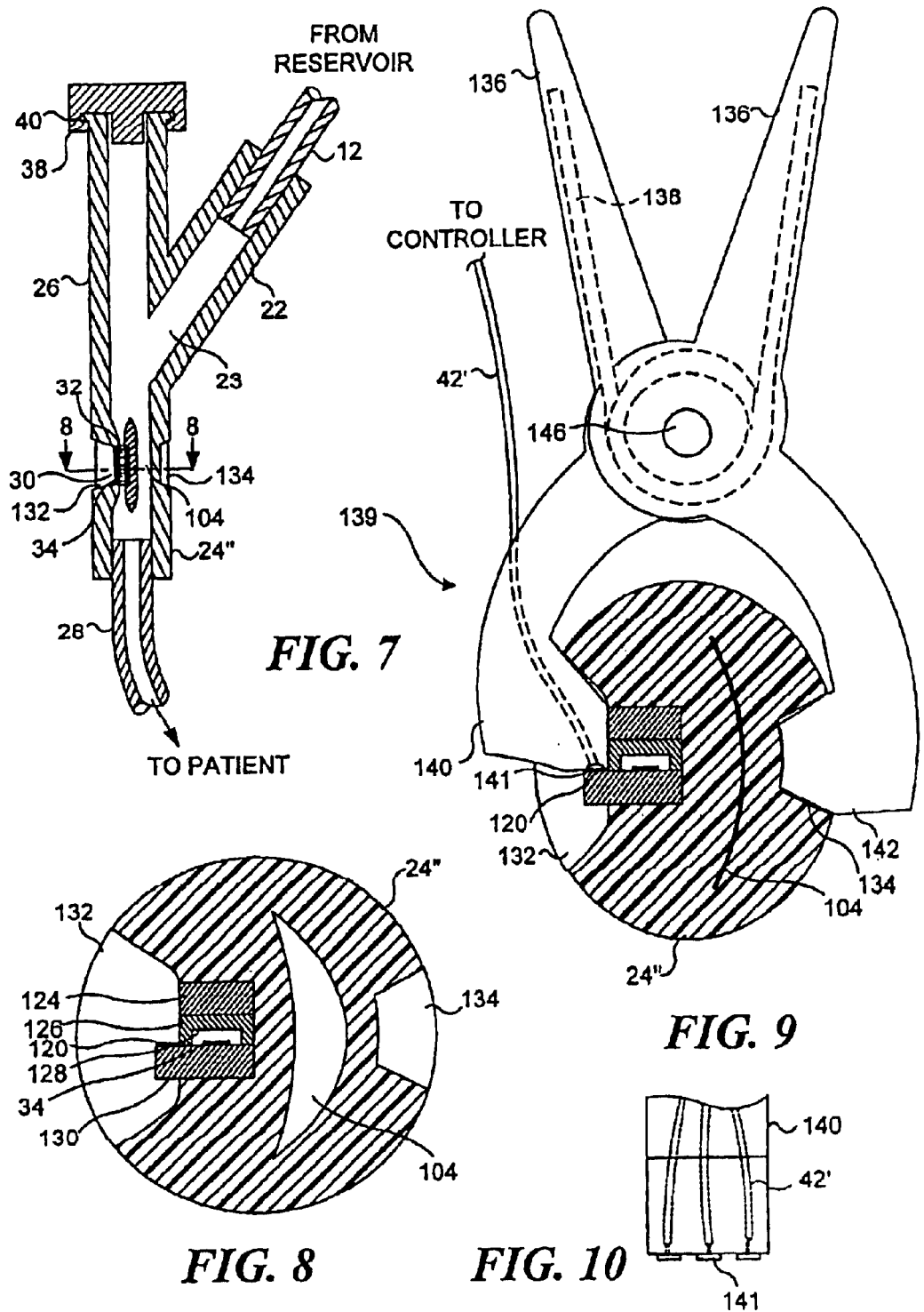

CLOSED-LOOP IV FLUID FLOW CONTROL

CROSS-REFERENCE TO RELATED APPLICATIONS

This is a continuation of U.S. patent application Ser. No. 09/628,846, filed Jul. 31, 2000, now U.S. Pat. No. 6,685,668 B1.

FIELD OF THE INVENTION

The invention generally concerns control of fluid flow rates, and more particularly concerns the control of fluid flow rate in intravenous fluid delivery systems.

BACKGROUND OF THE INVENTION

Intravenous (IV) fluid delivery systems are used to deliver fluids and medicines to patients at controlled rates. To more accurately control IV fluid delivery, an open-loop control system is typically used. A processor included in the open-loop control system varies the speed of a relatively accurate fluid pump used to infuse a medicinal fluid into a patient, based on a predefined algorithm and as a function of various parameters, such as temperature, fluid type, and desired flow rate. These open-loop processor-controlled pumping systems are generally expensive and complex. Usually, compensation for variations in pump accuracy must be employed in such systems to achieve an acceptable accuracy. The rate of fluid delivery is also affected by the precision of disposable components used in the fluid path that conveys a medicinal fluid to a patient. However, variations in the internal diameter and material hardness of fluid lines and pumping component comprising the disposable components, both initially, and as a result of changes over their period of use, cannot readily be compensated in an open-loop control algorithm. As a result, higher cost disposable components that are guaranteed to meet tight tolerance specifications must be used in such systems to avoid loss of accuracy.

Accordingly, it will be apparent that it would be desirable to provide a relatively low cost, low complexity system for delivery of medicinal fluids. A closed-loop system in which a desired parameter is measured to control the system can provide the required accuracy. For example, in a closed-loop system, it would be preferable to measure flow with a low cost flow sensor and to control an inexpensive fluid delivery pump based upon the measured flow rate, so as to achieve a desired flow rate. Previously, measurement of fluid flow has generally been prohibitively expensive in medicinal fluid infusion systems. However, the development of low cost flow sensors have made it much more practical and economical to monitor fluid flow in order to control a medical infusion system.

Low cost pumps can be used in a closed-loop system medicinal fluid infusion system, since the accuracy of the pump is not important in achieving a desired delivery rate. Similarly, the tolerance specifications for the disposable components used in the system can be greatly relaxed, because the precision of these components will no longer be of much concern. Also, most of the variables that must be considered in algorithms currently employed for open-loop control can be ignored in a closed-loop controlled infusion system. Consequently, the process control logic used in a closed-loop infusion system is relatively simple.

SUMMARY OF THE INVENTION

In accord with the present invention, a fluid delivery system is defined for infusing a medicinal fluid supplied from a reservoir into a patient at a desired rate. The fluid delivery system includes a fluid line through which the medicinal fluid is conveyed from the reservoir to a patient, and a flow controller that selectively varies a rate of flow of the medicinal fluid through the fluid line. A processor is controllably coupled to the flow controller and to a flow sensor that monitors a rate of flow of the medicinal fluid through the fluid line, producing an output signal that is indicative thereof. The processor responds to the output signal and operates the flow controller in a closed-loop process, to achieve the desired rate of infusion of the medicinal fluid into a patient.

In one preferred form of the invention, the flow sensor includes an orifice disposed in a fluid path through which the medicinal fluid flows in the fluid line, and the orifice has a cross-sectional size that is substantially less than that of the fluid line. A pressure-sensing module in the fluid line is configured to sense a pressure drop across the orifice, producing the signal indicative of flow rate. In one embodiment, the pressure sensing module includes a distal pressure sensor and a proximal pressure sensor, the distal pressure sensor being used for monitoring a distal pressure of the medicinal fluid, downstream of the orifice, and the proximal pressure sensor being used for monitoring a proximal pressure of the medicinal fluid, upstream of the orifice. A difference between the distal pressure and the proximal pressure signals is indicative of the rate of flow of the medicinal fluid through the fluid line.

In another embodiment, the pressure sensing module includes a differential pressure sensor that monitors a differential pressure across the orifice and in response thereto, produces the signal supplied to the processor, which is indicative of the rate of flow of medicinal fluid through the fluid line.

Preferably, the flow sensor is disposed in a "Y" fitting in the fluid line. In one embodiment, the flow sensor is removably coupled to the processor through a connector. In another embodiment, the flow sensor is removably coupled to the processor.

In some cases, it will occasionally be desirable to provide a substantially greater flow of medicinal fluid that can be achieved through the orifice of the flow sensor, e.g., to prime the fluid line before connecting it to a patient. In this case, a bypass channel is provided within the fitting, generally in parallel with the orifice. The bypass channel is then selectively opened to enable the medicinal fluid to substantially bypass the orifice when a greater rate of flow of the medicinal fluid than the desired rate is required through the fluid line.

One preferred form of the invention employs a pump for the flow controller, and the pump forces the medicinal fluid through the fluid line and into a patient. Alternatively, an electronically controlled valve is employed for the flow controller, the medicinal fluid flowing through the fluid line under the force of gravity.

A user interface is preferably included to enable input by a user of the desired rate of medicinal fluid flow through the fluid line.

Another aspect of the present invention is directed to a method for controlling a rate of infusion of a medicinal fluid into a patient through a fluid path. The method includes steps that are generally consistent with the functions performed by the elements discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 7 is a cross-sectional view of yet another embodiment of the Y site for the present invention, which includes a bypass channel;

FIG. 8 is a cross-sectional view of the embodiment of the Y site, taken along section line 8—8 in FIG. 7, and illustrating the bypass channel in its open state;

FIG. 9 is a cross-sectional view of the Y site shown in FIGS. 7 and 8, illustrating the use of a clamp that includes electrical contact on one jaw and which is employed for closing the bypass flow channel and for electrically connecting to a pressure sensor in the Y site;

FIG. 10 is an elevational view of an end portion of one of the jaws of the clamp shown in FIG. 9, illustrating the electrical contacts and leads provided thereon.

DESCRIPTION OF THE PREFERRED EMBODIMENT

Figure 1:
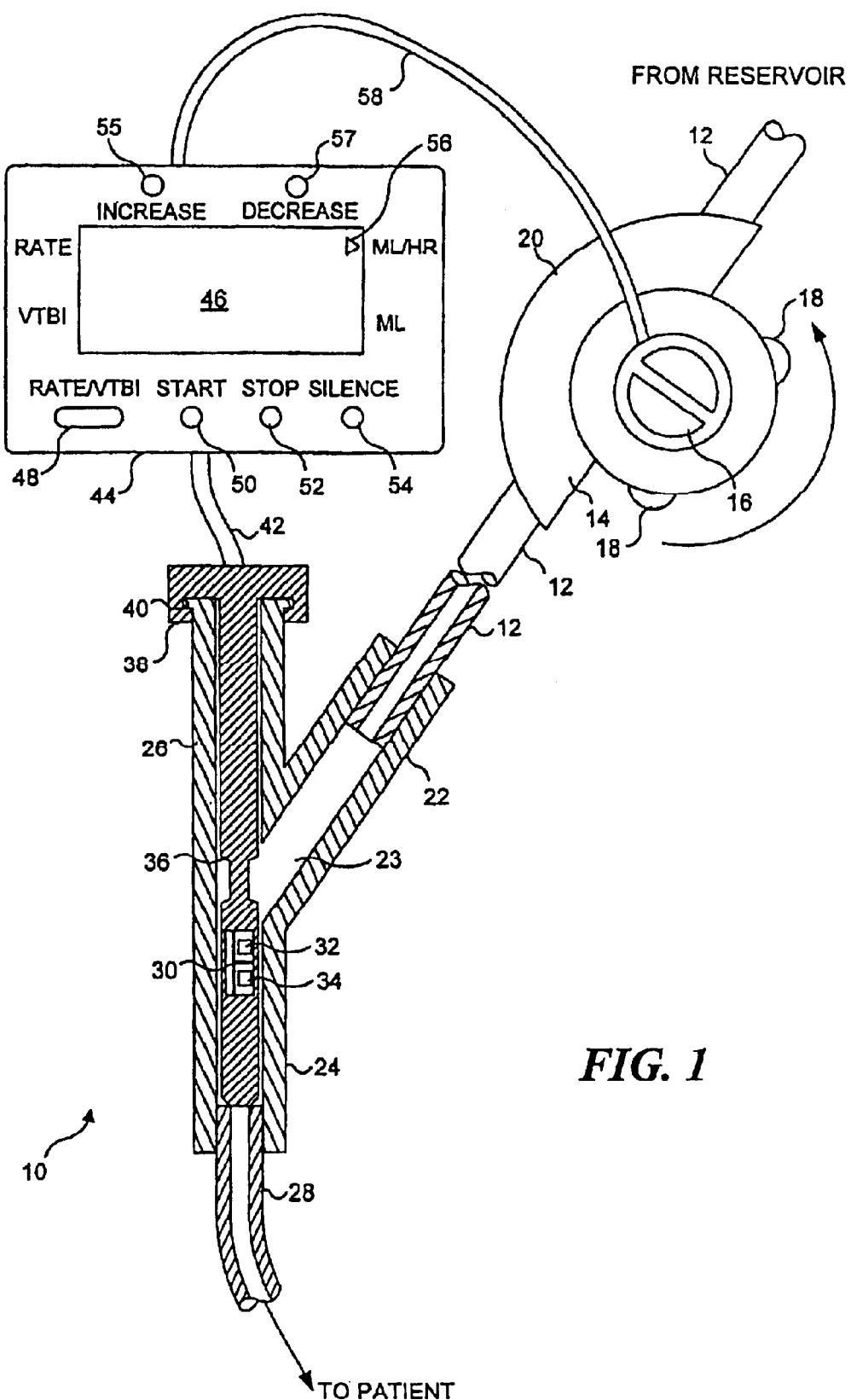
FIG. 1 is an elevational view of a portion of IV tube set and a first embodiment of the present invention, showing a cross-sectional view of a Y site that is provided with a flow sensor, which produces a signal for use in controlling a pump in a closed-loop process.

Several different embodiments of systems suitable for administering a medicinal fluid at a desired rate are illustrated in the Figures and are described below. A first such embodiment of a system 10 is shown in FIG. 1. System 10 includes a fluid line 12 that extends from a reservoir (not shown in this FIGURE) through a peristaltic pump 14. Peristaltic pump 14 comprises a plurality of rollers 18 that are driven along in a circular path by an electric motor 16 (or other suitable prime mover) in a rotational direction as indicated by the curved arrow. As is common in most such peristaltic pumps, rollers 18 periodically contact and compress fluid line 12, as the rollers move along the circular path, forcing successive boluses of a medicinal fluid through the fluid line for infusion into a patient (not shown). Fluid line 12 extends within the concave portion of a curved guide 20 against which rollers 18 act to compress the fluid line in pumping the medicinal fluid. However, it should be pointed out that many other types of pumps can be used in connection with the present invention.

One of the advantages of the present invention is that it enables a relatively inexpensive peristaltic pump or other type of pump, which may be of a relatively low accuracy in maintaining a desired rate of delivery, to be used, since the pump is directly controlled in a closed-loop process to achieve the desired delivery rate of the medicinal fluid to the patient. To control the rate at which peristaltic pump 14 infuses a medicinal fluid, the speed of electric motor 16 is varied so as to achieve the desired rate for delivery of the medicinal fluid by the pump. Further details of system 10 that enable the pump (i.e., its prime mover) to be controlled in this manner to achieve the desired rate of fluid flow are described below.

Fluid line 12 connects to an upper arm 22 of a Y site 24. The outlet of the Y site is connected to a fluid line 28 that conveys the medicinal fluid flowing under the urging of peristaltic pump 14 into the body of a patient at an infusion site. It should be noted, however, that in the present invention, peristaltic pump 14 (or other low cost pump) can be disposed either proximal or distal to the Y site. The medicinal fluid flows through a cavity 23 formed within the Y site to reach fluid line 28.

A flow-sensing module 36 is disposed within an upper arm 26 of Y site 24 and extends into the lower portion of the Y site. Fluid-sensing module 36 includes a solid state flow sensor 30 that comprises a proximal pressure sensor 32 and a distal pressure sensor 34. The proximal and distal pressure sensors are disposed on opposite sides of a restriction or orifice (shown more clearly in FIG. 5). By monitoring the proximal and distal pressure at points on opposite sides of the restriction or orifice of known cross-sectional size, flow sensor 30 determines the rate of flow of medicinal fluid through Y site 24, and thus through the fluid path into the patient. Flow-sensing module 36 is retained within Y site 24 by a flange 38, which sealingly engages a lip 40 formed on the upper end of arm 26.

A cable 42 connects the signal produced by flow sensor 30 to a controller 44. Controller 44 includes a display 46 on which either the volume or the rate of medicinal fluid infusion is displayed. Details of the controller are discussed below, in connection with FIG. 11. The user interface on controller 44 includes a switch 48 that switches between a display of the rate of fluid delivery in ml/hr and the volume to be infused (VTBI) in ml. Also provided on the controller are start and stop buttons 50 and 52, a button 54 for silencing alarms such as occur when an out-of-fluid condition or air bubble is detected in the fluid line, and buttons 55 and 57 for enabling a user to respectively increase and decrease displayed values being input for the desired VTBI and the desired rate of fluid delivery.

It should be noted that the flow-sensing module can be disposed in elements of the fluid line other than a Y site. For example, a portion of the fluid line can simply include a flow monitoring module that is sufficiently low in cost to be disposed of after use with a single patient. Several different techniques are shown herein for electrically connecting the flow sensing module to controller 44 or its equivalent.

Controller 44 responds to the proximal pressure and distal pressure signals received from flow sensor 30, deriving a flow signal therefrom corresponding to their difference, and the difference in pressures sensed on opposite sides of the restriction or orifice is indicative of the rate of flow of medicinal fluid through Y site 24 and into the patient. Based upon the monitored rate of flow of the medicinal fluid, which comprises a feedback signal, controller 44 implements a closed-loop control process by varying the speed of motor 16, and thus, the speed of peristaltic pump 14 to achieve the desired rate of flow of the medicinal fluid being infused. If the monitored rate of flow exceeds the desired rate of flow of the medicinal fluid, controller 44 causes motor 16 driving peristaltic pump 14 to slow sufficiently to the desired rate of infusion. Conversely, if the monitored rate of flow is less than the desired rate of flow of the medicinal fluid, the controller causes the motor to speed up, thereby increasing the rate at which peristaltic pump 14 is infusing the medicinal fluid sufficiently to achieve the desired rate.

Figure 2:
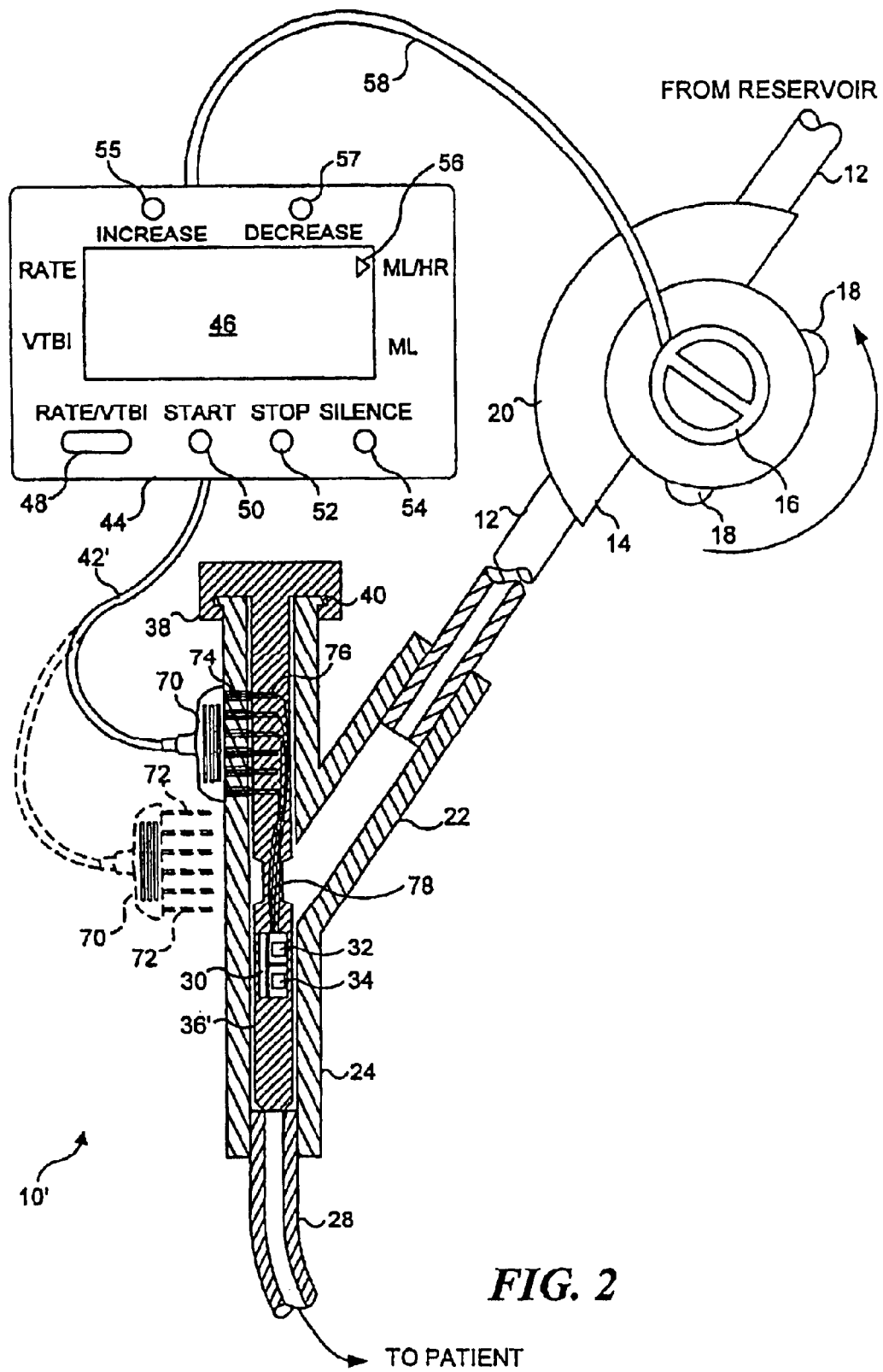
FIG. 2 is an elevational view of a portion of an IV tube set much like that of FIG. 1, but showing an embodiment that includes a connector for coupling a flow sensor to a controller.

In FIG. 2, a system 10' is illustrated and is similar in most respects to system 10. However, in system 10', a cable 42' includes a multi-pin connector 70 for electrically connecting to flow sensor 30, which comprises a portion of a flow sensing module 36' in which the flow sensor is connected through internal leads 78 to connector 70. Cable 42' and connector 70 are considered non-disposable and can be detached from flow sensor 30 and Y site 24. In almost all other respects, system 10' is identical to and includes equivalent elements to the embodiment shown in FIG. 1.

Connector 70 includes a plurality of conductive pins 72 that are inserted into corresponding orifices 74 formed in the side of the upper tube of the Y site. Pins 72 make electrical contact with corresponding female receptacle 76, which is connected to flow sensor 30 through internal leads 78 that extend through the interior of flow-sensing module 36'. The distal and proximal pressure signals determined by flow sensor 30 are conveyed through lead 78 and cable 42' to controller 44 for use in controlling peristaltic pump 14 (or other device for varying the rate of flow of the medicinal fluid, as explained herein), to achieve the desired rate of flow of the medicinal fluid into a patient.

Figures 3A, 3B:
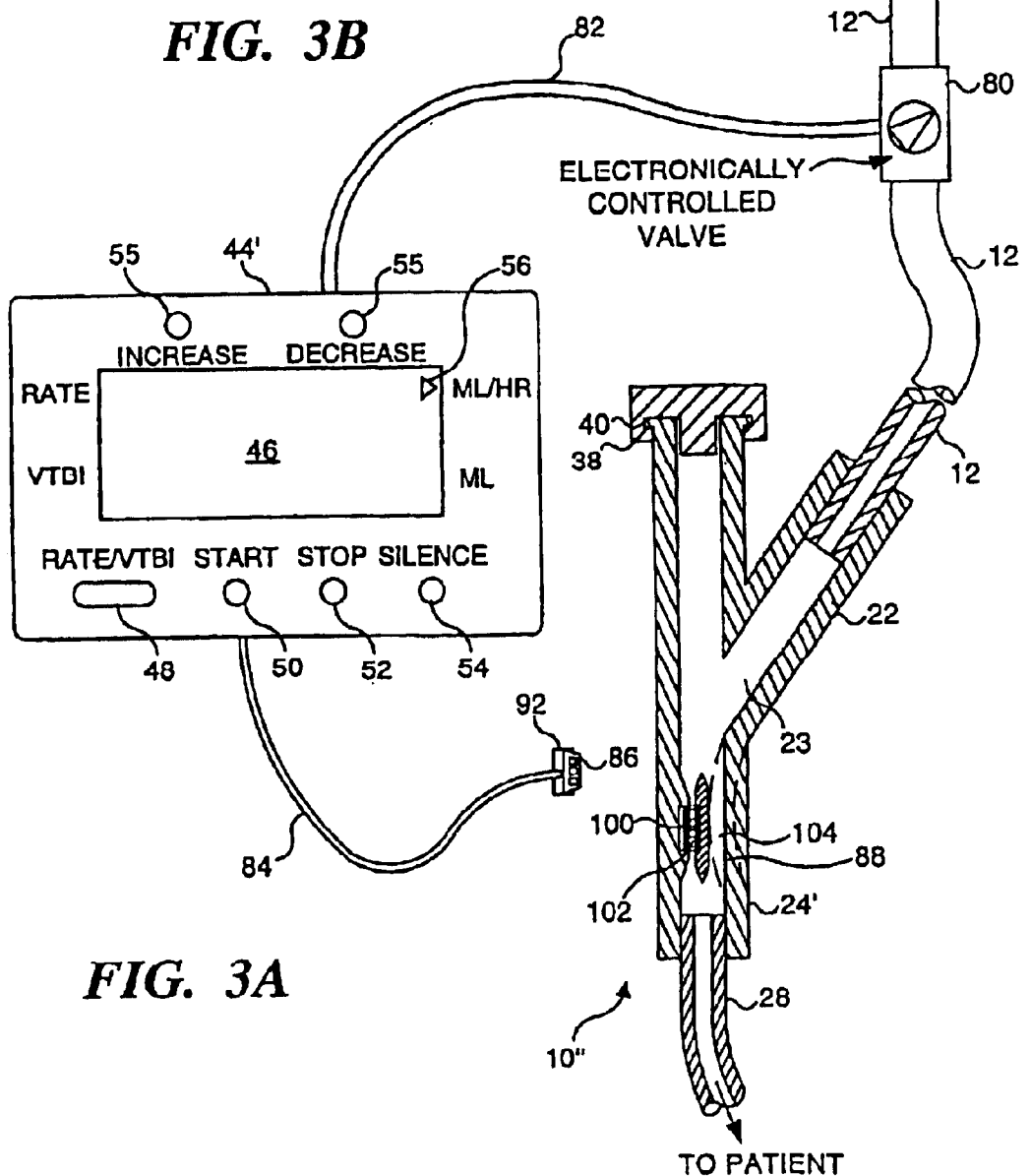
FIG. 3A is an elevational view of an embodiment that includes an electronically controlled valve for varying fluid flow rate and which includes a bypass around a flow sensor in a Y site.
FIG. 3B is a cross-sectional view of the flow sensor, showing the bypass path around the flow sensor, in the Y site shown in FIG. 3A.

FIGS. 3A and 3B illustrate further details of a system 10", comprising yet another embodiment of the present invention. In system 10", there are several differences compared to the previous two embodiments. For example, an electronically controlled valve 80 is used to vary the flow rate of a medicinal fluid 85 from a reservoir 83, which is disposed at a substantially higher elevation than a patient's body (not shown). The pressure head thus developed is sufficient to infuse the medicinal fluid at more than the desired rate. However, electronically controlled valve 80 modulates the rate of flow of medicinal fluid 85 from reservoir 83 to achieve the desired rate. A controller 44' provides a control signal that is conveyed to electronically controlled valve 80 through a cable 82. The control signal causes the electronically controlled valve to adjust the flow of the medicinal fluid to achieve the desired rate of infusion. The controlled flow of medicinal fluid 85 flows through fluid line 12 into a Y site 24', which includes an embedded differential pressure sensor 98 for monitoring the rate of flow of the medicinal fluid flow through the Y site. Differential pressure sensor 98 monitors the difference between a pressure at a distal point 102 and a proximal point 100, producing a signal for the differential pressure that is indicative of the rate of flow of the medicinal fluid flow through a restriction or orifice, which is disposed between the points at which the distal and proximal pressures are measured. Further details of the differential pressure sensor and of a probe 92 are illustrated in FIG. 3B. The power signal and the signal indicative of differential pressure are conveyed through a lead 84 that extends between controller 44' and probe 92, which has a plurality of spaced-apart contacts 86 that are sized and configured to couple with corresponding contacts (pads) on differential pressure sensor 98 when the probe is seated in an index notch 94 formed in the side of the Y-site adjacent to differential pressure sensor 98, so that the signal indicative of flow through the differential pressure sensor is conveyed to controller 44'.

Also shown in FIGS. 3A and 3B are details of a bypass passage 104 that extends generally parallel to the fluid path through the restriction or orifice within differential sensor 98 and for receiving the signal that it produces corresponding to the differential pressure between the proximal and distal points. Normally, bypass passage 104 is clamped shut while Y site 24' is being used for monitoring the flow of medicinal fluid 85 to a patient and is only opened in the event that a substantially greater rate of flow is required, for example, to flush the fluid line or to initially prime the fluid line, before connecting it to the patient. FIGS. 3A and 3B show bypass passage 104 open, but FIG. 3A also illustrates a dash line showing how the elastomeric material, i.e., a polymer of other plastic material, comprising Y site 24 is compressed with a suitable clamp (not shown) that holds probe 92 in place within index notch 94, with contacts 86 electrically mating with the corresponding contacts on the differential pressure sensor. The clamp will thus close bypass passage 104 when the Y site is being used to monitor the rate of medicinal fluid flow into a patient.

In each of the preferred embodiments, including the one shown in FIGS. 3A and 3B, the pressure sensors or differential pressure sensors can be fabricated as a capacitor, with one plate coupled to a substrate and an opposite, overlying plate supported in sealed relationship above the plate on the substrate, so that a vacuum exists between the two plates, enabling absolute pressure to be measured. In differential pressure sensor 98, an orifice would be provided to couple the volume between the two plates to the point that is distal the orifice or restriction, while the plate overlying the plate supported by the substrate would be exposed to the pressure of the medicinal fluid proximate the orifice or restriction. Alternatively, piezoelectric type pressure sensors can be used for the two pressure sensors in flow sensor 30 and for differential pressure sensor 98.

Figure 4:
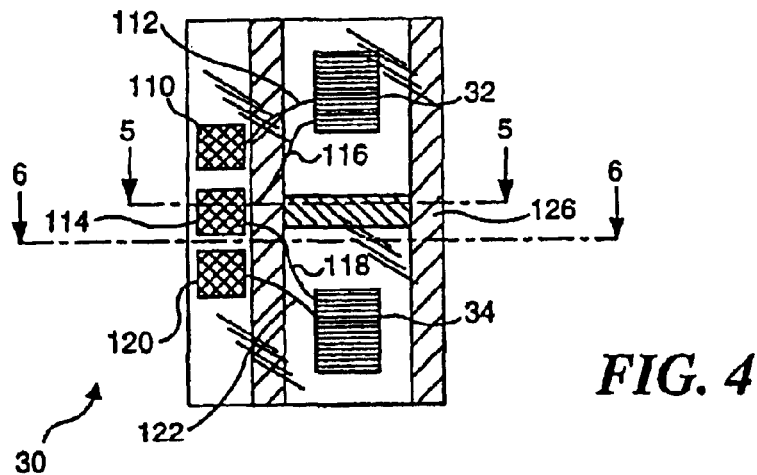
FIG. 4 is an enlarged elevational view of a flow sensor having proximal and distal pressure sensors for sensing proximal and distal pressures across an orifice.
Figure 5:
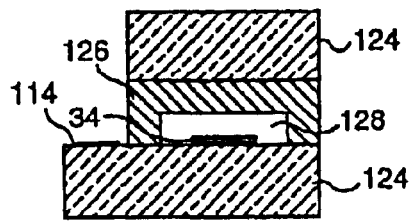
FIG. 5 is a cross-sectional view of the flow sensor of FIG. 4, taken along section line 5—5 in FIG. 4.
Figure 6:
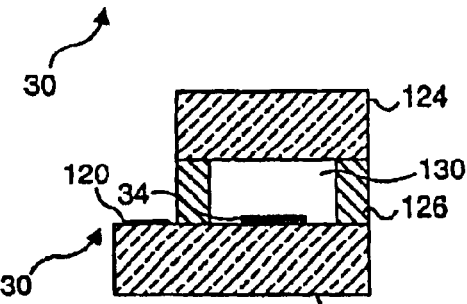
FIG. 6 is a cross-sectional view of the flow sensor of FIG. 4, taken along section line 6—6 in FIG. 4.

Further details of flow sensor 30 are illustrated in FIGS. 4–6. As will be evident particularly in FIGS. 5 and 6, flow sensor 30 includes a pair of glass slabs 124, disposed on opposite sides of a silicon spacer 126 that defines the fluid path through the flow sensor. Furthermore, silicon spacer 126 forms a restriction or orifice 128 that separates proximal pressure sensor 32 from distal pressure sensor 34, as shown in FIG. 4. The substantially smaller cross-sectional area of the restriction or orifice within flow sensor 30 is shown in FIG. 5, in contrast to the much greater area of a fluid passage 130 on opposite sides of the restriction. Pressure sensors 32 and 34 are fabricated on the larger of the pair of glass slabs 124 using conventional lithographic techniques, as are often used in fabricating integrated circuits. Furthermore, proximal pressure sensor 32 is connected through leads 112 and 116 to pads 110 and 114 on the larger of the glass slabs 124, pad 114 being a common terminal for both the proximal and distal pressure transducers. Likewise, distal pressure transducer 34 is connected through leads 118 and 122 to pads 114 and 120, which are also disposed on the exposed portion of the larger of the pair of glass slabs 124. While leads 112, 116, 118, and 122 are shown as discrete wires to simplify the drawings, it will be understood that these "wires" preferably comprise conductive traces applied to the larger one of glass slabs 124 using a conventional photolithographic technique, which is also employed to form pads 110, 114, 120. It will be understood that other suitable materials can be employed in fabricating proximal, distal, or differential pressure sensors, using much the same configuration disclosed above.

In a preferred embodiment, restriction or orifice 128 within pressure sensor 30 and in differential pressure sensor 98 is substantially smaller in cross-sectional area that that of fluid paths 130 on both the distal and proximal sides of the orifice or restriction. Those of ordinary skill in the art will appreciate that the dimensions used for the orifice and fluid paths can readily be varied, so long as the restriction provided by the orifice is substantially less than the cross-sectional areas of the proximal and distal fluid passages on opposite sides of the orifice, to ensure that a sufficiently great differential pressure is monitored as a result of the pressure drop of medicinal fluid flowing through the restriction or orifice to enable accurate control of the pump or electronically controlled valve that varies the flow rate of the medicinal fluid.

Another embodiment of a Y site 24" is illustrated in FIGS. 7–9. Y site 24" also includes bypass passage 104, but includes flow sensor 30 with the two separate pressure sensors, instead of differential pressure sensor 98. To connect to flow sensor 30, a clamp 139 is provided as shown in FIG. 9. A series of three spaced-apart electrical contacts 141 are included on the end of a jaw 140 on clamp 139 and the spacing between contacts 141 and their disposition correspond to the spacing between pads 110, 114, and 120 on flow sensor 30. Thus, each of electrical contacts 141 can readily make electrical connection with a different one of the pads. Connected to each of contacts 141 is a different one of a plurality of leads 42'. Leads 42' extend to controller 44 and convey the signals produced by the proximal and distal pressure sensors in flow sensor 30 to the controller.

To ensure that contacts 141 correctly meet and make contact with pads 110, 114, and 120 on flow sensor 30, clamp 139 also includes a jaw 142 shaped to fit within an index groove 134 provided on the side of Y site 24", disposed adjacent flow sensor 30, but opposite a recess 132. Jaw 140 is thus indexed to fit within recess 132, bringing contacts 141 into electrically conductive connection with pads 110, 114, and 120. Alternatively, the indexing function can be accomplished by providing the indexing geometry of jaw 142 and index groove 23 on jaw 140 and recess 132. Furthermore, clamp 139 includes handles 136 and a torsion spring 138 that is enclosed therein and which extends around a pivot 146 that couples the handles together. Torsion spring 138 provides a biasing force sufficient to compress the elastomeric material comprising Y site 24" so as to close bypass passage 104 as shown in FIG. 9.

It will be understood that other techniques for providing a probe configured for making electrical contact with pads 110, 114, and 120 on pressure sensor 30 can alternatively be used, and that such a probe or stylus can be held in place by a separate clamp that closes bypass passage 104. As noted above, when bypass passage 104 is closed, fluid flows through the fluid path and orifice or restriction within flow sensor 30, enabling a signal to be produced by the flow sensor indicative of the rate of the medicinal fluid flow therethrough, which is used by the controller in determining the rate at which the medicinal fluid is being infused into the patient. This feedback signal is used by the controller to achieve a desired rate of infusion, and for monitoring the total amount of medicinal fluid infused into a patient, to achieve a desired VTBI.

Figure 11:
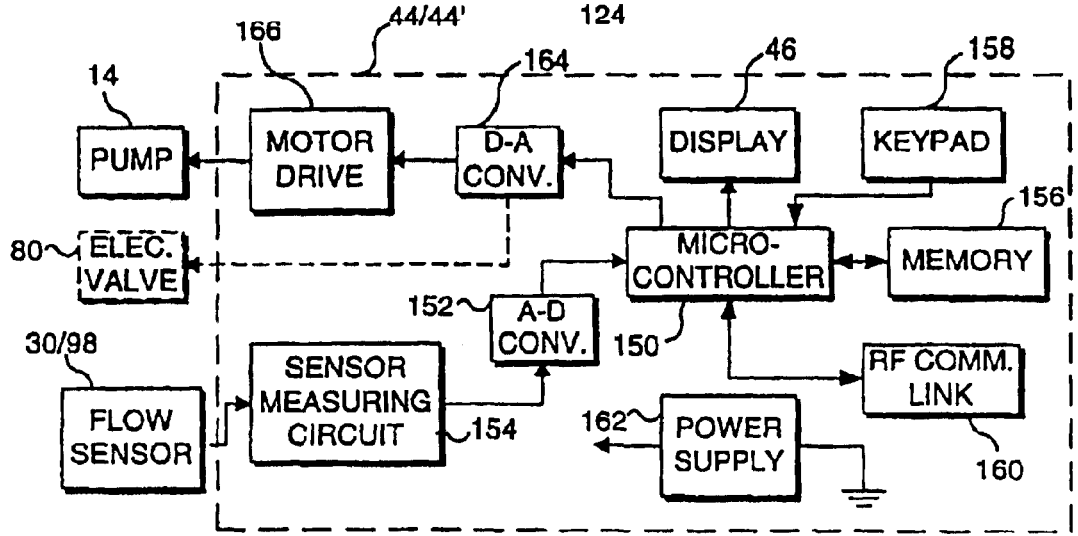
FIG. 11 is a functional block diagram of the controller, illustrating the components included therein.

FIG. 11 illustrates internal functional components of controllers 44/44'. Flow sensor 30 or differential pressure sensor 98 are connected to an appropriate sensor measuring circuit 154 having an output coupled to an analog-digital (A-D) converter 152. A-D converter 152 converts the analog signals supplied by the sensor measuring circuit into a digital signal that is input to a microcontroller 150. As a further alternative, microcontroller 150 may include its own internal A-D converter, in which case A-D converter 152 can be omitted.

Microcontroller 150 is connected to a memory 156 (or may alternatively include an internal memory) that comprises both random access memory (RAM) and read only memory (ROM)—neither separately shown. Machine instructions stored within memory 156 are used to implement control functions when executed by microcontroller 150. A keypad 158 comprising the buttons on the user interface of controllers 44/44' enables user to control the microcontroller functions. The microcontroller drives display 46, which indicates the values of the parameters selected by the user with keypad 158. A radio frequency (RF) communication link 160 is optionally provided, enabling microcontroller 150 to communicate with external devices (not shown) via an RF transmission. The communication with such external devices is likely to be bi-directional, enabling input of desired parameters to alternatively be provided by an external device instead of via keypad 158. A power supply 162 provides the appropriate voltage levels for each of the components comprising controller 44 or controller 44'.

Microcontroller 150 produces an output signal that is applied to a digital-to-analog (D-A) converter 164. The D-A converter changes the digital signal from microcontroller 150 to a corresponding analog signal that is applied to a motor drive block 166. It should also be noted that microcontroller 150 may include an internal D-A converter, enabling D-A converter 164 to be omitted. Also, it is contemplated that a motor drive 166 responsive to digital signals may be employed, also obviating the need for the D-A converter. As an alternative, if electrically-controlled valve 80 is used instead of peristaltic pump 14 to vary the flow of medicinal fluid through the fluid line to the patient, the digital signal from the microcontroller or the analog signal from D-A converter 164 may be used to control the electrically-controlled valve. When peristaltic pump 14 is used, motor drive 166 provides the drive signal to the electric motor that drives the pump to vary the rate at which the medicinal fluid is infused into the patient.

By monitoring the rate of flow of a medicinal fluid using flow sensor 30 or differential pressure sensor 98, a feedback signal (i.e., the signal indicative of the current rate of flow of the medicinal fluid received from the Y site) is produced. Microcontroller 150 uses the feedback signal to control peristaltic pump 14 or electrically controlled valve 80 to achieve the desired rate selected by the user.

Although the present invention has been described in connection with the preferred form of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

What is claimed is:

1. A flow sensor device for monitoring a fluid flow through a fluid line to a patient, comprising:

a flow sensor adapted to be disposed in a fluid path of a medicinal fluid flowing through a fluid line, said flow sensor producing a signal indicative of a rate of flow of a medicinal fluid through the fluid path, said flow sensor includes an orifice disposed in the fluid path, said orifice having a cross-sectional size that is substantially less than that of the fluid path, both proximal and distal to the orifice, and a pressure-sensing module configured to sense a pressure drop across the orifice, said pressure-sensing module producing the signal in response thereto;

wherein the pressure sensing module further comprises a distal pressure sensor and a proximal pressure sensor, said distal pressure sensor monitoring a distal pressure of the medicinal fluid, downstream of the orifice, and said proximal pressure sensor monitoring a proximal pressure of the medicinal fluid, upstream of the orifice, a difference between the distal pressure and the proximal pressure determining the signal supplied to a processor, which is indicative of the rate of flow of medicinal fluid through the fluid line.

2. The flow sensor device of claim 1 wherein the flow sensor is disposable and is coupled into the fluid path.

3. The flow sensor device of claim 1 further comprising a bypass channel within the fluid line, generally in parallel with the orifice, said bypass channel being selectively opened to enable the fluid to substantially bypass the orifice when a substantially greater rate of flow of the fluid than the desired rate is required through the fluid line.

4. The flow sensor device of claim 3 wherein the flow sensor is disposed in a Y fitting in the fluid line and the bypass channel is within the Y fitting.

* * * * *